United States Patent
De Jong (10) Patent No.: US 10,539,683 B2
(45) Date of Patent: Jan. 21, 2020

(54) DEVICE AND METHOD FOR SIMULTANEOUS X-RAY AND GAMMA PHOTON IMAGING WITH A STACKED DETECTOR

(71) Applicant: KONINKLIJKE PHILIPS N.V., Eindhoven (NL)

(72) Inventor: Hugo Wilhelmus Antonius Maria De Jong, Zeist (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/742,701

(22) PCT Filed: Jul. 8, 2016

(86) PCT No.: PCT/NL2016/050503
§ 371 (c)(1),
(2) Date: Jan. 8, 2018

(87) PCT Pub. No.: WO2017/007326
PCT Pub. Date: Jan. 12, 2017

(65) Prior Publication Data
US 2018/0203131 A1    Jul. 19, 2018

(30) Foreign Application Priority Data
Jul. 9, 2015 (NL) .................................... 2015125

(51) Int. Cl.
G01T 1/161    (2006.01)
A61B 6/00    (2006.01)
G01T 1/164    (2006.01)

(52) U.S. Cl.
CPC .......... G01T 1/1615 (2013.01); A61B 6/4266 (2013.01); G01T 1/1612 (2013.01); G01T 1/1642 (2013.01)

(58) Field of Classification Search
CPC ... G01T 1/1615; G01T 1/1612; G01T 1/1642; A61B 6/4266
See application file for complete search history.

(56) References Cited

U.S. PATENT DOCUMENTS

| 4,179,100 A | 12/1979 | Sashin |
| 5,155,365 A * | 10/1992 | Cann .................... A61B 6/4241 250/363.02 |
| 5,401,969 A | 3/1995 | Basler |
| 6,429,433 B1 | 8/2002 | Gagnon |
| 6,448,559 B1 * | 9/2002 | Saoudi .................. G01T 1/1603 250/367 |

(Continued)

FOREIGN PATENT DOCUMENTS

| EP | 1325706 A2 | 7/2003 |
| WO | 2006123119 A1 | 11/2006 |

(Continued)

*Primary Examiner* — Christine S. Kim (57) ABSTRACT

A dual mode radiation detector includes an x-ray detector layer configured to convert incident x-ray radiation into x-ray electrical data, where the x-ray detector forms an incident face of the dual mode radiation detector. The dual mode radiation detector further includes a collimator disposed below the x-ray detector layer, and a gamma photon detector layer disposed below the collimator to convert incident gamma photons into gamma photon electrical data.

28 Claims, 3 Drawing Sheets

(56) References Cited

U.S. PATENT DOCUMENTS

| | | | |
|---|---|---|---|
| 2007/0085011 A1* | 4/2007 | Ritter | A61B 6/4441 |
| | | | 250/363.05 |
| 2007/0114426 A1 | 5/2007 | Tkaczyk | |
| 2008/0242980 A1* | 10/2008 | Lees | G01T 1/161 |
| | | | 600/436 |
| 2010/0260316 A1 | 10/2010 | Stein | |
| 2014/0048713 A1* | 2/2014 | Liu | G21K 1/025 |
| | | | 250/366 |
| 2015/0320375 A1* | 11/2015 | De Jong | A61B 6/032 |
| | | | 378/63 |

FOREIGN PATENT DOCUMENTS

| | | | |
|---|---|---|---|
| WO | 2007105942 | A2 | 9/2007 |
| WO | 2012066469 | A1 | 5/2012 |
| WO | 2014092574 | A1 | 6/2014 |

\* cited by examiner

DEVICE AND METHOD FOR SIMULTANEOUS X-RAY AND GAMMA PHOTON IMAGING WITH A STACKED DETECTOR

CROSS-REFERENCE TO PRIOR APPLICATIONS

This application is the U.S. National Phase application under 35 U.S.C. § 371 of International Application No. PCT/NL2016/050503, filed on Jul. 8, 2016, which claims the benefit of Netherlands Application No. 2015125, filed on Jul. 9, 2015. These applications are hereby incorporated by reference herein.

The invention relates to the field of medical imaging, more particularly to detectors for medical imaging suitable for the simultaneous x-ray and nuclear imaging.

X-ray imaging and nuclear imaging are central techniques in the field of medical imaging.

In X-ray imaging an x-ray detector, e.g. a scintillator, detects x-ray radiation from an x-ray source, e.g. an x-ray tube. Said x-ray detector is positioned such that it detects the x-ray radiation that is transmitted through the patient.

In nuclear imaging a radio-active isotope is injected into the patient. A gamma detector detects the gamma photons that arise from the decay of said radio-active isotope.

In the field of medical imaging there is an interest in combining x-ray imaging with gamma photon imaging into dual mode imaging devices, as the x-ray image reveals anatomical structures that facilitate interpretation of the nuclear image. For instance, the location of a tumour imaged with a radio-active isotope can be determined more precisely if is location with respect to the neighbouring bone structure is known. This bone structure is imaged by x-rays.

In order to extract said anatomical and functional information, said x-ray detector and gamma detector should acquire images of the same region of interest. While this can be done with both detectors offset to one another, e.g. adjacent to one another, it is preferred that both detectors have the same orientation with respect the region of interest.

Moreover, it is desired to acquire x-ray and gamma photon images simultaneously, as this strongly enhances the usefulness of combining said x-ray and gamma photon images. For instance, a patient may move, and also movement within the body, e.g. beating of the heart and subsequent movement of e.g. arteries, may hinder interpretation of combined images if taken sequentially at such a slow pace that significant movement during the sequential acquisition occurs.

Detectors of the type described above that comprise two layers for simultaneous x-ray and gamma photon detectors are described for instance in in WO2012066469, that describes a PET-CT system. The x-ray detector forms the incident face of the detector, and the gamma detector is placed behind said x-ray detector. The x-ray detector is transparent to part of the gamma photons, which then impinge upon the gamma detector.

The device of WO2012066469 is not entirely satisfactory.

The present invention aims to provide an improved stacked detector for simultaneous x-ray and gamma photon imaging.

To this end the invention proposes a dual mode radiation detector comprising:

an x-ray detector layer to convert x-ray radiation into x-ray electrical data, said x-ray detector forming an incident face of said dual mode radiation detector;
a collimator disposed below the x-ray detector layer; and
a gamma photon detector layer disposed below the collimator to convert gamma photons into gamma photon electrical data.

The inventive radiation detector thus comprises a collimator placed in between the x-ray detector layer and the gamma photon detector layer. This collimator is a plate or body with parallel sides that only transmits part of the incident gamma photon flux, and is e.g. used for selecting gamma photons that originate from a region of interest. Said collimators are well-known in the field of nuclear imaging and are usually made of tungsten or lead as these materials are good absorbers of gamma photons. Different types of collimators are known, e.g. parallel hole collimators, pinhole collimators or cone beam collimators.

The stacked detector of WO2012066469, that lacks a collimator disposed below the x-ray detector layer, requires a large number of images to be taken under different acquisition positions of the detector with respect to the object of interest to obtain functional information from nuclear imaging. Therefore imaging with the device of WO2012066469 is time-consuming and involves complex image reconstruction.

The inventive radiation detector is considered optimally suited for obtaining a gamma emission or functional image from gamma photon electrical data acquired at a single, e.g. stationary, acquisition position of the detector with respect to the object of interest. Said gamma emission image is then fused using suitable software and a computer with an x-ray image reconstructed from x-ray electrical data acquired simultaneously with said gamma photon electrical data.

The approach to obtain fused x-ray and nuclear images using a stationary acquisition position of the detector system is also employed and described in more detail in WO2014092574. In embodiments the detector of the present invention may replace the detector arrangement of WO2014092574.

During stationary acquisition the x-ray equipment and the dual mode radiation detector are held static such that an x-ray image and gamma radiation image, which images are to be fused into a fused image that is to be displayed, are obtained in a fully stationary situation, so without the data acquisition for each image requiring any motion of the x-ray equipment and dual mode radiation detector or parts thereof relative to the object to be examined, e.g. relative to the patient.

Simultaneous detection of x-ray radiation and gamma photon radiation with said inventive radiation detector at a single stationary acquisition position thus has the potential to provide quicker and simpler imaging.

In some embodiments the x-ray detector, collimator and gamma detector are stacked directly on top of each other. Such an arrangement provides for a compact detector. For example the stack is embodied as a unit to the placed in an imaging installation, e.g. a C-arm device, a gantry device, etc.

In embodiments an x-ray filter layer is arranged between the x-ray detector layer and the collimator. Preferably said filter layer is transparent to gamma photons. For example said filter layer contains Tin (Sn).

In embodiments the x-ray detector layer, x-ray filter layer, collimator, and gamma photon detector layer are stacked directly on top of each other.

In some embodiments the areas of the x-ray detector, optional x-ray filter layer, collimator and gamma detector that face the patient are all equal. In other words, the frontal area of the collimator and gamma photon detector layers each equal that of the incident face of said dual mode radiation detector. In this way the region from which radiation is detected is substantially the same for both detectors.

In embodiments the dual mode radiation detector may be provided with different collimators, e.g. parallel hole collimators and cone beam collimators. Said cone beam collimator may have its focal spot at the location of the x-ray source. In a preferred embodiment is cone beam collimator is provided having a focal spot that is offset from the focal spot of the x-ray source, e.g. at least one centimetre, e.g. several centimetres, laterally offset from the focal spot of the x-ray source. This reduces the passing of X-ray through the collimator and thus reduces the x-ray load on the gamma detector.

In embodiments the collimator may be removable and insertable into said dual mode radiation detector.

For example the detector may be embodied to move the x-ray detector layer and the gamma detector somewhat apart for insertion, laterally, of a selected collimator between them, e.g. with or without an x-ray filter layer, with the dual mode detector further being embodied to bring said stacked components into a compacted stack configuration, e.g. with components close to each other or even clamped against one another.

For example the dual mode detector comprises a frame or housing wherein said stacked components are retained. For example the housing has an open front exposing the incident face of the stack, and a radiation shielding circumferential wall and bottom covering the sides of the stack and the bottom.

X-ray detection in the inventive dual mode radiation detector may take place in various ways. For instance, the x-ray detector layer may be an indirect flat panel detector comprising a scintillator layer and behind said scintillator layer a detector array containing photodiodes. Said scintillator layer converts the incoming x-rays into photons, which photons after propagation to the photodiodes are converted to an electrical signal.

Said scintillator layer may for instance comprise a caesium iodide scintillator with a layer thickness of 10-3000 microns, e.g. 300 μm, and behind said scintillator an array of thin silicon-based film transistor with thickness of approximately 0.1-10 mm, e.g. 700 μm.

Said x-ray detector is transparent to at least part of the gamma photons.

The incident face of the dual mode detector x-ray layer is preferably planar.

Similarly, the gamma detector of the inventive dual mode radiation detector can be of various types. For instance the collimator and gamma photon detector layer form a gamma camera. Said gamma camera comprises said collimator, a scintillator layer and below said scintillator layer a photomultiplier layer. Said scintillator layer converts the incoming gamma photons to scintillation light, which is then converted to an electrical signal in the photomultiplier layer.

Said gamma photon scintillator may be a sodium iodide based scintillator, possibly sodium iodide with thallium doping, with thickness of 1-50 mm, e.g. 9.5 mm.

The gamma detector may comprises a semi-conductor detector design, preferably a CZT (cadmium zinc telluride) detector or cadmium telluride detector.

In an embodiment the collimator disposed between the x-ray detector layer and gamma photon detector layer is the only collimator of the dual mode radiation detector and said x-ray detector layer is fully exposed to the x-ray radiation transmitted through the object to be imaged.

In another embodiment an anti-scatter grid is provided in front of the x-ray detector. Anti-scatter grids are known in the field of x-ray imaging and are used to reduce the amount of scattered x-ray radiation incident upon the x-ray detector layer, while transmitting x-ray radiation that has not been scattered while propagating from the x-ray source to the anti-scatter grid. Provision of an anti-scatter grid enhances the resolution of the x-ray image reconstructed from said x-ray electrical data.

Different types of anti-scatter grids, e.g. parallel or focussed grids, may be used. In order to change between anti-scatter grids in some embodiments said anti-scatter grid is removable from the dual mode radiation detector.

It is preferred that any anti-scatter grid is configured to transmit at least part, e.g. the majority, of the gamma photons incident on said anti-scatter grid. The anti-scatter grid can then remain in place during acquisition of gamma photon electrical data.

To further prevent the erroneous interpretation of x-ray photons incident on the gamma photon detection layer as gamma photon detection event, the energy of the photons incident on the gamma photon detection layer may be measured and said energy values may form part of the gamma photon electrical data. Energy values different from those expected for gamma photons are then filtered out during further processing of said gamma photon electrical data.

Moreover, to prevent the pile up of x-ray photons onto the gamma photon detector a gamma photon detector with a short decay time, e.g. shorter than that of the often-used sodium iodide scintillator layers can be used. Such a short decay time may be achieved by using a scintillation crystal comprising lutetium yttrium orthosilicate or lanthanum tribromine ($LaBr_3$).

The invention also relates to a dual mode radiation detecting system, said system comprising a dual mode radiation detector as described herein and an image processing unit. Said image processing unit receives both the x-ray electrical data and gamma photon electrical data from the dual mode radiation detector. The image processing unit is adapted to fuse simultaneously acquired x-ray electrical data and gamma photon electrical data into fused images containing both x-ray electrical data and gamma photon electrical data.

Said image processing unit is adapted to reconstruct x-ray images and gamma emission images from said x-ray electrical data and gamma photon electrical data respectively. Said processing unit is adapted to consider the collimator geometry in said reconstruction of gamma emission images from gamma photon electrical data. Optionally also the anti-scatter grid is considered in said reconstruction. However, in general considering the anti-scatter grid is not needed, as at least part of the gamma photons are not hindered by said anti-scatter grid.

In practice two or three x-ray photons may be simultaneously absorbed by the gamma photon detector layer. The combined energy of said x-ray photons may be similar to that of a gamma photon. Thus, further measures may be needed to prevent x-ray photons to be interpreted as gamma photons by said gamma photon detector layer. This may be done by means of x-ray source adapted to emit pulses of x-ray radiation, e.g. with a duration of between 1 and 10 ms. The detection of gamma photons by the gamma photon detector layer may then be performed, if desired, only in between x-ray radiation pulses, or said pulsing of the x-ray radiation being taken into account in the analysis of gamma photon electrical data, e.g. removing from said data any data representing gamma photon detections during said x-ray radiation pulses.

As preferred x-ray pulses and a gamma photon detection interval with a duration much shorter than any movement (of the patient, or of for instance the heart through its beating), is used, and then no displacement of the imaged region in between an x-ray detection interval and an gamma photon detection interval is foreseen, so that fusing both images is still expected to give the abovementioned benefits. This rapid sequential imaging, during which the object is essentially stationary, is therefore also considered simultaneous. Such duration of x-ray pulse, x-ray detection and gamma photon detection interval is preferably at most within 0.5 s.

The dual mode imaging system may further comprise a support installing supporting said x-ray source and said dual mode radiation detector. Said support installation is adapted to provide a stationary acquisition position of the x-ray source and dual mode radiation detector. The x-ray electrical data and gamma photon electrical data that are fused into fused images containing structural and functional information can be obtained with the x-ray source and dual mode radiation detector in a stationary acquisition position.

The invention also relates to a dual mode imaging system comprising a dual mode radiation detector as described herein, an image processing unit, and an x-ray source, e.g. an x-ray tube, wherein the image processing unit is adapted to receive both the x-ray electrical data and gamma photon electrical data from the dual mode radiation detector. This system further comprises a rotating gantry which defines a subject receiving aperture, e.g. with a support table for a person, wherein the rotating gantry is adapted to rotate, e.g. over a full revolution(s), about the subject receiving aperture about an axis of rotation, e.g. a horizontal axis. The x-ray source is mounted to the rotating gantry for rotation therewith and a detector head is mounted to the rotating gantry for rotation therewith, wherein the detector head is mounted opposite the x-ray source, e.g. at diametrically opposed locations relative to the subject receiving space. The detector head comprises the inventive dual mode radiation detector in order to receive x-rays from the x-ray source as well as to receive gamma photon radiation from a subject in the subject receiving aperture.

The use of the inventive dual mode detector in combination with the rotating gantry for example facilitates the correction of the obtained image for any motion of a part, e.g. organ, of the subject during image acquisition by rotating the gantry around the subject. The gantry can also be operated stepwise, so that stationary acquisitions are possible during each standstill. Also the described pulsed mode operation of the x-ray source and related gamma photon data interpretation may be combined with a gantry installation.

For example the inventive dual mode detector can be of use in a gantry system and methods as described in U.S. Pat. No. 6,429,433.

In another embodiment the support installation may be a C-arm, e.g. as described in more detail in WO201409257. In the embodiment envisioned here said dual mode radiation detector is supported by or mounted onto the second free end segment of the C-arm.

The inventive dual mode radiation detecting system may be configured for simultaneous fluoroscopy and scintigraphy, that is, the formation of 2D images.

The dual mode radiation detector may be part of a C-arm device, a device employed in the field of x-ray and/or nuclear imaging of patients.

In a common design such a C-arm device comprises:
a C-arm having opposed first and second free segments,
a C-arm support structure connected to said C-arm intermediate said first and second free end segments,
an x-ray source mounted on said first free end segment of the C-arm and adapted to emit an x-ray beam in an x-ray beam direction, and
an x-ray detector mounted on said second free end segment, so that an x-ray beam emitted by said x-ray source in said beam direction is imaged onto said x-ray detector.

A more detailed description and possible embodiments of a C-arm device are given in WO2014092574.

The dual mode radiation detector may be incorporated into a C-arm device by replacing the x-ray detector by the dual mode radiation detector to obtain a C-arm dual mode imaging device. A method for such conversion of an existing C-arm device into a dual mode imaging C-arm device is comprised in this application.

Moreover, existing C-arm devices with a detector other than the inventive dual mode radiation detector may be retrofitted with said inventive dual mode radiation detector.

The invention also relates to a method for simultaneous x-ray imaging and nuclear imaging comprising the steps of:
providing an object containing a radioactive isotope that emits gamma photons;
providing an x-ray source adapted to emit x-ray radiation towards said examination region;
providing one or more dual mode radiation detectors as described herein, said radiation detectors adapted to detect x-ray radiation emitted by said x-ray source, e.g. x-ray radiation transmitted through said object, and to detect gamma photons emitted by said radioactive isotope within said object;
acquiring simultaneously x-ray electrical data and gamma photon electrical data with said dual mode radiation detector;
processing said x-ray electrical data and gamma photon electrical data to reconstruct x-ray images and gamma emission images, respectively; and
fusing x-ray images and gamma emission images of simultaneously acquired x-ray electrical data and gamma photon electrical data into fused x-ray and gamma photon images.

For example the method comprises a mammographic examination of a breast of a female patient.

To prevent x-ray photon spill over of the gamma photon detector layer, the x-ray source may emit short pulses of x-ray radiation, e.g. 1-10 ms pulses, wherein the gamma detector acquires gamma photon electrical data in between said short x-ray radiation pulses. Thus, the invention also comprises a method for simultaneous x-ray and nuclear imaging, said method comprising providing one or more dual mode radiation detectors and a pulsed x-ray source, wherein acquiring gamma photon electrical data precedes or follows acquiring x-ray photon electrical data. The duration of the acquisition of both x-ray photon electrical data and gamma photon electrical data is preferably 0.5 s or less, so that the object is essentially stationary during the acquisition of both x-ray electrical data and gamma electrical data that are fused into an image.

In some embodiments, the x-ray electrical data and gamma electrical data that are fused into fused images containing x-ray electrical data and gamma photon electrical data are acquired with said x-ray source and dual mode radiation detector in a stationary acquisition position. Said stationary acquisition position may achieved by a C-arm device.

In some embodiments, a single set of simultaneously acquired x-ray electrical data and gamma photon electrical data at a single stationary acquisition position may be sufficient to reconstruct an x-ray image and a gamma emission image that are fused into an image containing anatomical and functional information.

In some embodiments, after one or more fused images have been obtained at a certain stationary acquisition position of the detector, a different stationary acquisition position is chosen to obtain more fused images. However, to obtain functional images and fused images a single stationary acquisition position suffices.

The inventive dual mode detector and discussed methods may be applied to two-dimensional imaging, that is, the x-ray imaging is fluoroscopic imaging and the nuclear imaging is scintigraphic imaging. By choosing different stationary acquisition positions as described above also three-dimensional imaging may be performed.

The invention will now be discussed with reference to the drawings. In the drawings.

The elements of these drawings are not scaled, that is, no information can be found in the relative dimensions of elements of these drawing.

With reference to the drawings embodiments and optional features of the dual mode radiation detector will be described.

Figure 1:
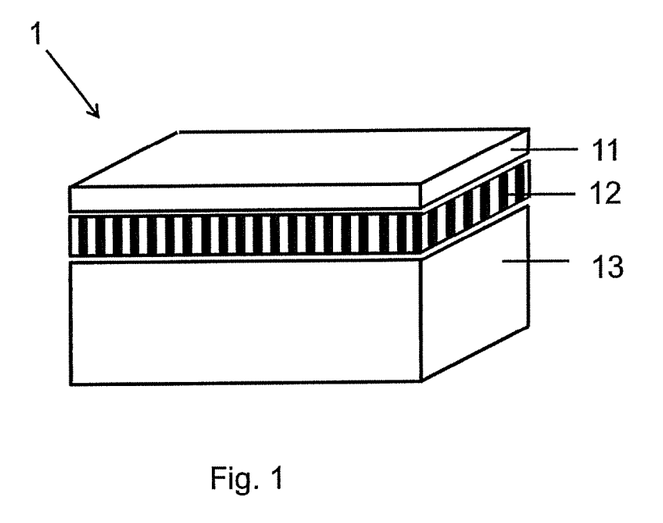
FIG. 1 shows a side view of a dual mode radiation detector according to the invention.

FIG. 1 shows a dual mode radiation detector 1 comprising an x-ray detector layer 11. Said x-ray detector 11 forms the incident face of said dual mode radiation detector. A collimator 12 is disposed below said x-ray detector 11 and a gamma photon detector layer is disposed below said collimator 12.

In the shown embodiment collimator 12 is a parallel hole collimator. However, the use of other types of collimators, such as a cone beam collimator, is also envisioned as is discussed with reference to FIG. 3.

Figure 2:
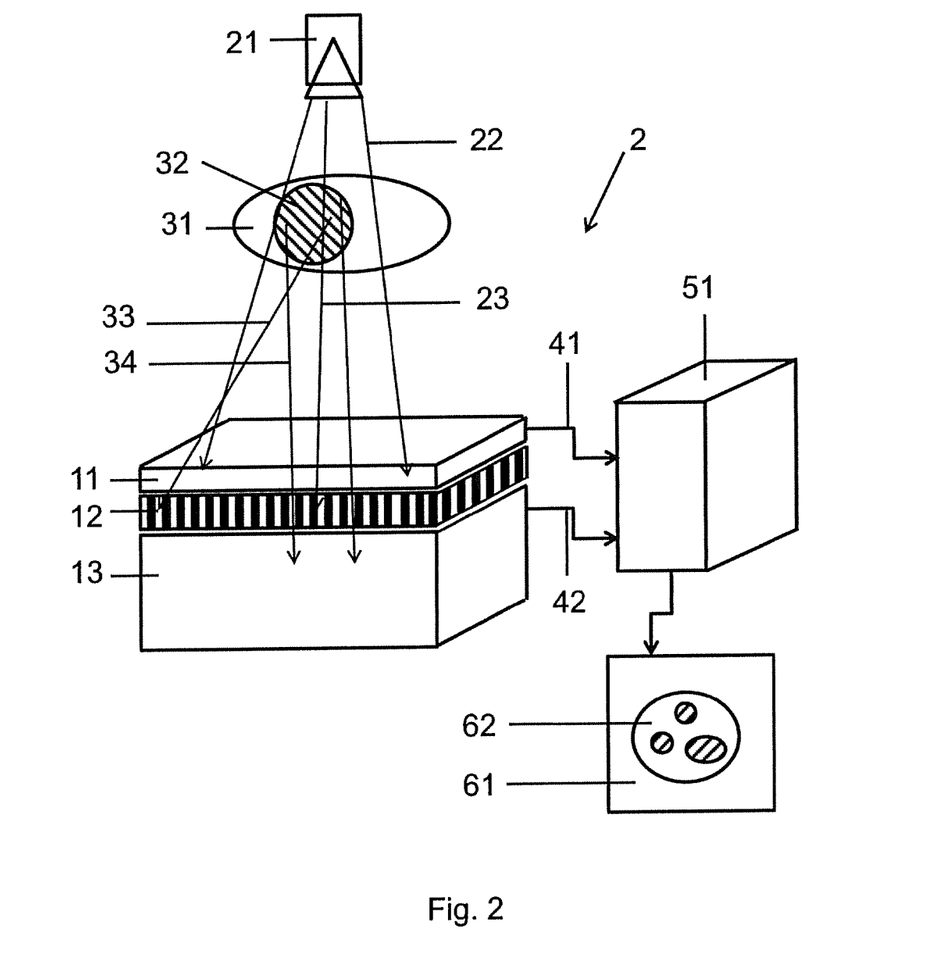
FIG. 2 shows a side of a dual mode radiation detecting system according to the invention.

FIG. 2 shows a dual mode radiation detecting system 2. The dual mode radiation detecting system comprises 2 a dual mode radiation detector 1 according to the invention, said dual mode radiation detector comprising an x-ray detector layer 11, a collimator 12 and an gamma photon detector 13 layer in that order.

Said x-ray detector layer 11 outputs x-ray electrical data 41 comprising information e.g. on the time, location and energy associated with detections. Furthermore, gamma photon detector layer 13 outputs gamma photon electrical data 42 comprising information e.g. on the time, location and energy associated with detections.

Furthermore, FIG. 2 shows an x-ray source 21, e.g. an x-ray tube, that emits x-ray radiation 22 in the direction of a patient 31. Said x-ray radiation is partly transmitted through said patient, e.g. rays 22 and 23, and impinges upon the detector 1 at the incident face thereof. Said radiation is partly absorbed in x-ray detector 11, e.g. ray 22, and partly transmitted by said x-ray detector and subsequently absorbed by the collimator 12. Alternatively, but not shown, rays may be transmitted by the x-ray detector and collimator, and may be absorbed by the gamma photon detector.

A radioactive isotope is present in a region 32 of the patient 31. Said isotope emits gamma photons, e.g. photons 33 and 34. Said photons may be transmitted by the x-ray detector. Subsequently they may be pass the collimator, e.g. photon 34, and may be absorbed by the gamma photon detector. If their direction of propagation differs from the alignment of the collimator apertures, they may also be absorbed by said collimator as is here the case for photon 33.

Said dual mode radiation detecting system 2 further comprises an image processing unit 51 that receives the x-ray electrical signal 41 and gamma photon electrical 42. Said image processing unit constructs based on the x-ray electrical signal 41 an x-ray image and reconstructs, based on the gamma photon electrical data 41 and considering the characteristics of the collimator 12, a gamma photon emission image.

Subsequently, the x-ray transmission image and gamma photon from simultaneously detected x-ray radiation and gamma photon radiation can be fused into a single fused image 62 and said fused image displayed on a display 61.

Figure 3:
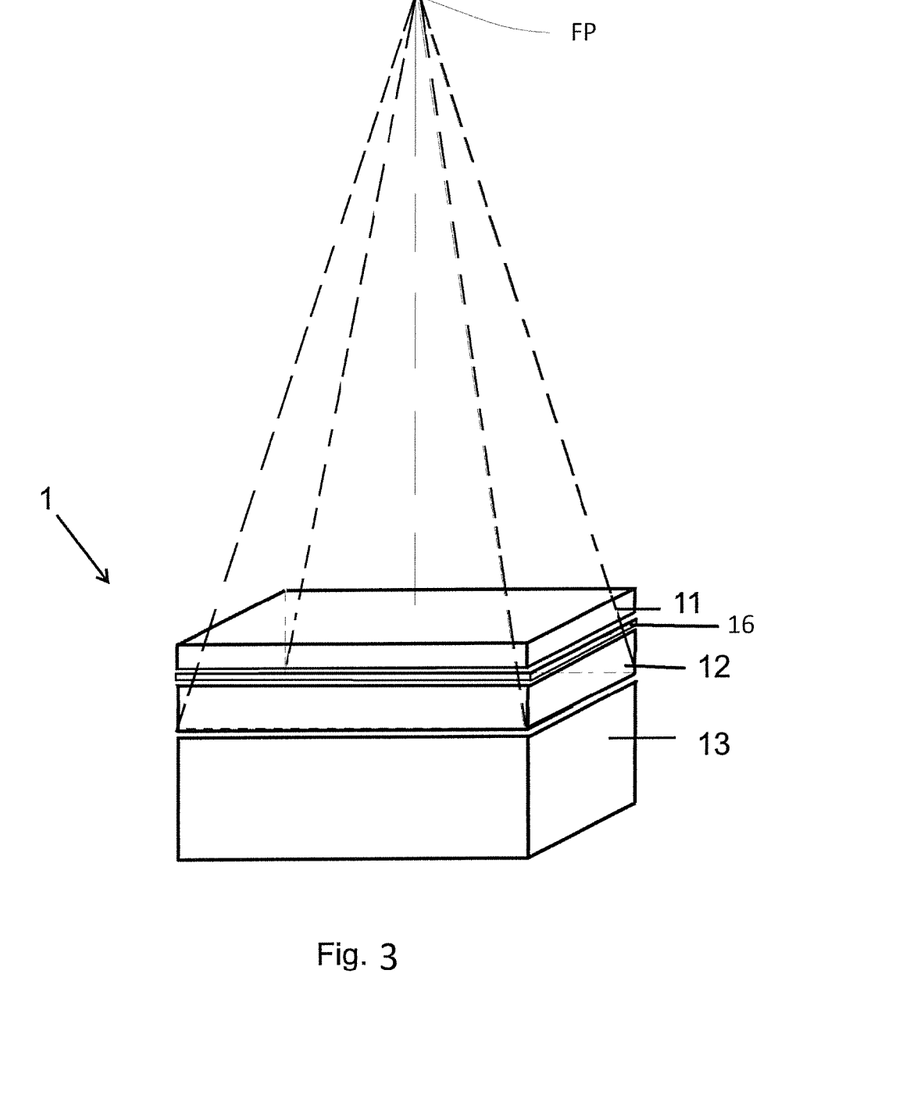
FIG. 3 shows a side view of another dual mode radiation detector according to the invention.

FIG. 3 shows a dual mode radiation detector 1 composed of components that are stacked directly onto one another.

An x-ray detector layer 11 forms the incident face of the dual mode radiation detector.

Below said x-ray detector layer, as is optional, there is an x-ray filter layer 16, e.g. made of or comprising Tin (Sn). The layer 16 is preferably designed to filter out x-rays whilst being transparent to gamma photons.

A collimator 12 is disposed below the x-ray detector 11, and here also below the x-ray filter layer.

As schematically indicated, and as preferred, the collimator is a cone beam collimator having a focal spot FP.

Below the collimator 12 a gamma photon detector layer 13 is disposed.

As explained it may be advantageous to arrange and/or embody the detector 1 with cone beam collimator 12 such that is focal spot FP is offset, e.g. laterally, from the focal spot of the x-ray source. This reduces/avoids penetration of x-ray through the collimator, which may be advantageous for the operation of the detector layer 13.

For example the radiation detector comprises a support structure, e.g. a skeletal frame, wherein these components are stacked and secured, e.g. removable from the frame, e.g. allowing to exchange one component for an alternative version of said component and/or allowing to arrange or dispense with the filter layer 16.

The invention claimed is:

1. A dual mode radiation detector comprising:
an x-ray detector layer configured to convert incident x-ray radiation into x-ray electrical data, said x-ray detector layer forming an incident face of said dual mode radiation detector;
a collimator disposed below the x-ray detector layer;
an x-ray filter disposed between the x-ray detector layer and the collimator; and
a gamma photon detector layer disposed below the collimator and configured to convert incident gamma photons into gamma photon electrical data such that the collimator is between the x-ray detector layer and the gamma photon detector layer.

2. The dual mode radiation detector according to claim 1, wherein the x-ray detector layer, collimator and gamma photon detector layer are stacked on top of each other.

3. A dual mode radiation detector comprising:
an x-ray detector layer to convert incident x-ray radiation into x-ray electrical data, said x-ray detector layer forming an incident face of said dual mode radiation detector;
a collimator disposed below the x-ray detector layer; and a gamma photon detector layer disposed below the collimator to convert incident gamma photons into gamma photon electrical data, wherein an x-ray filter layer is arranged between the x-ray detector layer and the collimator, and wherein the x-ray detector layer, the x-ray filter layer, the collimator, and the gamma photon detector layer are stacked directly on top of each other.

4. The dual mode radiation detector according to claim 1, wherein frontal areas of the collimator and of the gamma photon detector layer each equals a frontal area of the incident face of said dual mode radiation detector.

5. The dual mode radiation detector according to claim 1, wherein said collimator is removable and insertable into said dual mode radiation detector.

6. The dual mode radiation detector according to claim 1, wherein the x-ray detector layer is an indirect flat panel detector comprising a scintillator layer and a detector array containing photodiodes below said scintillator layer.

7. The dual mode radiation detector according to claim 1, wherein the collimator and gamma photon detector layer form a gamma camera, said gamma camera comprising the collimator, a scintillator layer and a photomultiplier layer below said scintillator layer.

8. The dual mode radiation detector according to claim 7, wherein the collimator is a parallel hole collimator.

9. The dual mode radiation detector according to claim 8, further comprising an anti-scatter grid provided in front of the x-ray detector layer configured to reduce amount of scattered x-ray radiation incident upon the x-ray detector layer.

10. The dual mode radiation detector according to claim 9, wherein said anti-scatter grid is removable from said dual mode radiation detector.

11. The dual mode radiation detector according to claim 9, wherein said anti-scatter grid is configured to transmit at least part of the gamma photons and wherein said anti-scatter grid is configured to remain in place in front of the x-ray detector during acquisition of gamma photon electrical data.

12. The dual mode radiation detector according to claim 1, wherein the collimator is a cone beam collimator.

13. The dual mode radiation detector according to claim 1, wherein the collimator disposed between the x-ray detector layer and gamma photon detector layer is the only collimator of the dual mode radiation detector and wherein the incident face is fully exposed to radiation impinging on said dual mode radiation detector.

14. The dual mode radiation detector according to claim 1, wherein said gamma photon detector layer comprises a scintillator layer with a decay time shorter than that of sodium iodide scintillators with thallium doping by using a lutetium yttrium orthosilicate or lanthanum tribromine (LaBr$_3$) scintillation crystal.

15. A dual mode radiation detecting system, comprising:
a dual mode radiation detector, including:
an x-ray detector layer to convert incident x-ray radiation into x-ray electrical data, said x-ray detector layer forming an incident face of said dual mode radiation detector;
a collimator disposed below the x-ray detector layer;
an x-ray filter disposed between the x-ray detector layer and the collimator; and
a gamma photon detector layer disposed below the collimator to convert incident gamma photons into gamma photon electrical data; and an image processing unit, said image processing unit receiving both the x-ray electrical data and gamma photon electrical data from said dual mode radiation detector, and said image processing unit configured to fuse simultaneously acquired x-ray electrical data and gamma photon electrical data into fused images containing both the x-ray electrical data and the gamma photon electrical data.

16. The dual mode radiation detecting system according to claim 15, wherein the gamma photon electrical data comprises information on energy of photons incident on the gamma photon detector layer, and said image processing unit is configured to filter out x-ray photons incident on the gamma photon detector layer based on the energy of photons incident on the gamma photon detector layer.

17. The dual mode radiation detecting system according to claim 15, said system being configured for simultaneous fluoroscopy and scintigraphy.

18. The dual mode imaging system according to claim 15, comprising an x-ray source, wherein said gamma photon detector layer comprises a scintillator layer with a decay time shorter than that of sodium iodide scintillators with thallium doping by using a lutetium yttrium orthosilicate or lanthanum tribromine (LaBr$_3$) scintillation crystal.

19. The dual mode imaging system, comprising a dual mode radiation detector according to claim 15, comprising an x-ray source, said x-ray source having a focal spot, wherein said the collimator of said dual mode radiation detector is cone beam collimator having a focal spot that is offset from the focal spot of the x-ray source.

20. The dual mode imaging system, comprising a dual mode radiation detector according claim 15, comprising an x-ray source, said x-ray source being configured to emit pulses of x-ray radiation, wherein said gamma photon detector layer is configured to detect photons in between said pulses of x-ray radiation, wherein said x-ray electrical data is acquired during an x-ray pulse and said gamma photon electrical data is acquired before or after said x-ray pulse so that both the x-ray electrical data and the gamma photon electrical data are acquired within a time interval of 0.5 second and fused into the fused images containing both the x-ray electrical data and the gamma photon electrical data.

21. The dual mode imaging system according to claim 20, further comprising a support installation supporting said x-ray source and said dual mode radiation detector, said support installation being configured to provide a stationary acquisition position of the x-ray source and dual mode radiation detector, and wherein the x-ray electrical data and the gamma photon electrical data fused into said fused images are obtained with the x-ray source and the dual mode radiation detector in said stationary acquisition position.

22. The dual mode imaging system according to claim 21, wherein said support installation is a C-arm device, said C-arm device comprising:
a C-arm having opposed first and second free end segments; and
a C-arm support structure connected to said C-arm and located between said first and second free end segments,
wherein said x-ray source is supported by said first free end segment of the C-arm and configured to emit an x-ray beam in an x-ray beam direction, and
wherein said dual mode radiation detector is supported by said second free end segment, so that the x-ray beam emitted by said x-ray source in said beam direction is imaged onto said dual mode radiation detector.

23. A dual mode imaging system comprising a dual mode radiation detector according to claim 15, further comprising a rotating gantry which defines a subject receiving aperture, the rotating gantry being configured to rotate about the subject receiving aperture about an axis of rotation; the x-ray source being mounted to the rotating gantry for rotation therewith, a detector head being mounted to the rotating gantry for rotation therewith, the detector head being mounted opposite the x-ray source, the detector head comprising said dual mode radiation detector to receive x-rays from the x-ray source as well as to receive gamma photon radiation from a subject in said subject receiving aperture.

24. A C-arm dual mode radiation detecting device, comprising:
- a C-arm having opposed first and second free end segments;
- a C-arm support structure connected to said C-arm and located between said first and second free end segments;
- an x-ray source mounted on said first free end segment of the C-arm and configured to emit an x-ray beam in an x-ray beam direction; and
- a dual mode radiation detector, said dual mode radiation detector mounted on said second free end segment, so that an x-ray beam emitted by said x-ray source in said beam direction is imaged onto said dual mode radiation detector,
- wherein the dual mode radiation detector includes:
  - an x-ray detector layer configured to convert incident x-ray radiation into x-ray electrical data, said x-ray detector layer forming an incident face of said dual mode radiation detector;
  - a collimator disposed below the x-ray detector layer;
  - an x-ray filter disposed between the x-ray detector layer and the collimator; and
  - a gamma photon detector layer disposed below the collimator and configured to convert incident gamma photons into gamma photon electrical data such that the collimator is between the x-ray detector layer and the gamma photon detector layer.

25. A method for simultaneous x-ray and nuclear imaging comprising acts of:
- providing an object containing a radioactive isotope that emits gamma photons towards an examination region;
- providing an x-ray source adapted to emit x-ray radiation towards said examination region;
- providing one or more dual mode radiation detectors, said one or more dual mode radiation detectors being configured to detect x-ray radiation emitted by said x-ray source, and transmitted through said object, and to detect gamma photons emitted by said radioactive isotope within said object, each detector of said one or more dual mode radiation detectors including:
  - an x-ray detector layer configured to convert incident x-ray radiation into x-ray electrical data, said x-ray detector layer forming an incident face of said dual mode radiation detector;
  - a collimator disposed below the x-ray detector layer;
  - an x-ray filter disposed between the x-ray detector layer and the collimator; and
  - a gamma photon detector layer disposed below the collimator and configured to convert incident gamma photons into gamma photon electrical data such that the collimator is between the x-ray detector layer and the gamma photon detector layer;
- acquiring simultaneously x-ray electrical data and gamma photon electrical data with said dual mode radiation detector;
- processing said x-ray electrical data and said gamma photon electrical data to reconstruct x-ray images and gamma emission images, respectively; and
- fusing the reconstructed x-ray images and the reconstructed gamma emission images of simultaneously acquired x-ray electrical data and gamma photon electrical data into fused x-ray and gamma photon images.

26. The method according to claim 25, wherein said x-ray source is operated to emit pulses of x-ray radiation with a duration of between 1 and 10 ms, and wherein the x-ray electrical data is acquired during an x-ray pulse and the gamma photon electrical data is acquired before and/or after said x-ray pulse so that both the x-ray electrical data and the gamma photon electrical data for a fused image are acquired within a time interval of at most 0.5 second.

27. The method according to claim 25, wherein said x-ray electrical data and gamma photon electrical data fused into fused images are acquired with said x-ray source and said dual mode radiation detector in a stationary acquisition position.

28. The method according to claim 25, wherein the x-ray imaging is fluoroscopic imaging and the nuclear imaging is scintigraphic imaging.

* * * * *